US005790586A

United States Patent [19]

Hilton, Jr. et al.

[11] Patent Number: 5,790,586

[45] Date of Patent: Aug. 4, 1998

[54] METHOD AND APPARATUS FOR SIMULTANEOUSLY ILLUMINATING, VIEWING AND MEASURING THE TEMPERATURE OF A BODY

[75] Inventors: Albert R. Hilton, Jr.; Kenneth A. Klein. both of Richardson, Tex.

[73] Assignee: Amorphous Materials, Inc., Garland, Tex.

[21] Appl. No.: 130,098

[22] Filed: Sep. 30, 1993

[51] Int. Cl.⁶ .............. G01J 5/08; G01K 13/00; A61B 6/00

[52] U.S. Cl. .............. 374/131; 374/141; 374/124; 600/474

[58] Field of Search ............... 374/131, 141, 374/124, 121; 128/736, 664, 9, 6; 600/549, 474, 200, 108, 182

[56] References Cited

U.S. PATENT DOCUMENTS

| | | |
|---|---|---|
| 4,253,731 | 3/1981 | Anderson et al. ............ 385/142 |
| 4,343,182 | 8/1982 | Pompei ........................ 374/124 |
| 4,408,827 | 10/1983 | Guthrie et al. ............... 374/131 |
| 4,498,481 | 2/1985 | Lemke ......................... 128/736 |
| 4,567,881 | 2/1986 | Heller ........................... 128/9 |
| 4,583,526 | 4/1986 | Ali ............................... 128/6 |
| 4,666,245 | 5/1987 | Pointer ......................... 374/131 |
| 4,766,886 | 8/1988 | Juhn ............................. 128/9 |
| 4,794,619 | 12/1988 | Tregay ......................... 374/131 |
| 5,052,816 | 10/1991 | Nakamura et al. ........... 374/124 |
| 5,121,740 | 6/1992 | Uram ............................ 128/6 |
| 5,152,278 | 10/1992 | Clayman ....................... 128/6 |
| 5,183,031 | 2/1993 | Rossoff ......................... 128/6 |
| 5,210,814 | 5/1993 | McNally ....................... 128/6 |
| 5,213,093 | 5/1993 | Swindle ........................ 128/6 |
| 5,328,365 | 7/1994 | Jacoby ......................... 128/6 |
| 5,419,312 | 5/1995 | Arenberg et al. ............. 600/549 |

OTHER PUBLICATIONS

Michalski, L. et al., Temperature Measurement, published by John Wiley & Sons Ltd., pp. 152–153 (1991).

Primary Examiner—Diego F. F. Gutierrez
Attorney, Agent, or Firm—Locke Purnell Rain Harrell

[57] ABSTRACT

Temperature of a body is determined by measuring the infrared radiation emitted by the body while simultaneously viewing the body. The body is viewed through a viewing cone with visible wavelength light conducted to the body from a remote source by optical fibers. Infrared radiation emitted by the body is collected by infrared-transmitting fibers which conduct the infrared energy to a remote sensor.

4 Claims, 1 Drawing Sheet

METHOD AND APPARATUS FOR SIMULTANEOUSLY ILLUMINATING, VIEWING AND MEASURING THE TEMPERATURE OF A BODY

BACKGROUND OF THE INVENTION

This invention relates to the methods and apparatus for detecting and measuring infrared radiation to determine body temperature. More particularly, it relates to methods and apparatus for illuminating a body such as the tympanic membrane with visible wavelength energy so that the body can be optically viewed while properly orienting the apparatus so that infrared radiation from the body can be monitored to determine the body temperature indicative of such radiation.

It has long been known that the temperature of the tympanic membrane in the ear closely approximates the temperature of the hypothalamus gland which regulates body temperature. Accordingly, devices have been designed, developed and produced for quantitatively measuring the infrared radiation emitted by the tympanic membrane and using these measurements to compute and display measured body temperature. Determination of body temperature based on infrared radiation from the tympanic membrane is reasonably convenient and is highly desireable since the entire process is accomplished without physical contact with the membrane and body temperature is determined essentially instantaneously.

Devices for determining body temperature by measuring emitted infrared radiation basically comprise a window or lens which collects radiation in the 2 to 14 µm range and concentrates the emitted radiation on a detector, usually a thermopile or pyroelectric detector. The lens is usually placed at the end of a cone adapted to be positioned in the ear canal close enough to detect emitted infrared radiation without touching the membrane. Highly accurate temperature measurements are obtained if the cone is properly aligned. However, all ear canals are not shaped the same. Furthermore, the canal may have obstructions such as wax, etc. For these and other reasons, the operator can never be certain that the temperature reading obtained is accurate since the cone may be aimed to detect infrared radiation from body parts other than the tympanic membrane (such as the canal wall) or the optical path between the membrane and the detector may be obstructed by wax, etc. Since the cone carrying the infrared detection equipment occupies the ear canal, the operator cannot visually observe the tympanic membrane to ascertain that the infrared radiation measured is only that radiated by the tympanic membrane.

SUMMARY OF THE INVENTION

In accordance with the present invention, the difficulties and uncertainties of properly aligning the infrared detector to receive only radiation from the tympanic membrane are obviated by apparatus which provides a lens for optically viewing the tympanic membrane combined with apparatus for directing optical energy onto the tympanic membrane so that the membrane may be directly observed while simultaneously collecting infrared radiation from the membrane observed. Since the apparatus of the invention illuminates and permits viewing of the tympanic membrane while detecting infrared radiation therefrom, the operator may visually observe the target membrane and ascertain that only radiation from the target membrane is detected and that the optical path between the membrane and the detector is not obstructed. Accordingly, extremely accurate measurements of body temperature can be obtained substantially instantaneously with absolute certainty that the temperature being measured is, in fact, the temperature of the body desired. Other features and advantages of the invention will become more readily understood from the following detailed description taken in connection with the appended claims and attached drawing in which:

DESCRIPTION OF PREFERRED EMBODIMENTS

Commercial devices known as otoscopes are currently available for visual inspection of the tympanic membrane. The otoscope comprises a viewing cone aligned with a lens so that the operator may look through the lens and viewing cone to inspect the tympanic membrane. The otoscope includes a handle which usually includes an visible light source. Visible wavelength radiation from the light source is transmitted through optical fibers which conduct the light by internal reflection from the light source to the end of the viewing cone. Thus the operator may insert the viewing cone into the ear canal and illuminate the tympanic membrane while viewing the tympanic membrane through the lens and viewing cone. The present invention combines the general principles of the otoscope with infrared-detecting apparatus which detects and measures infrared energy radiating from the object viewed through the otoscope.

Figure 1:
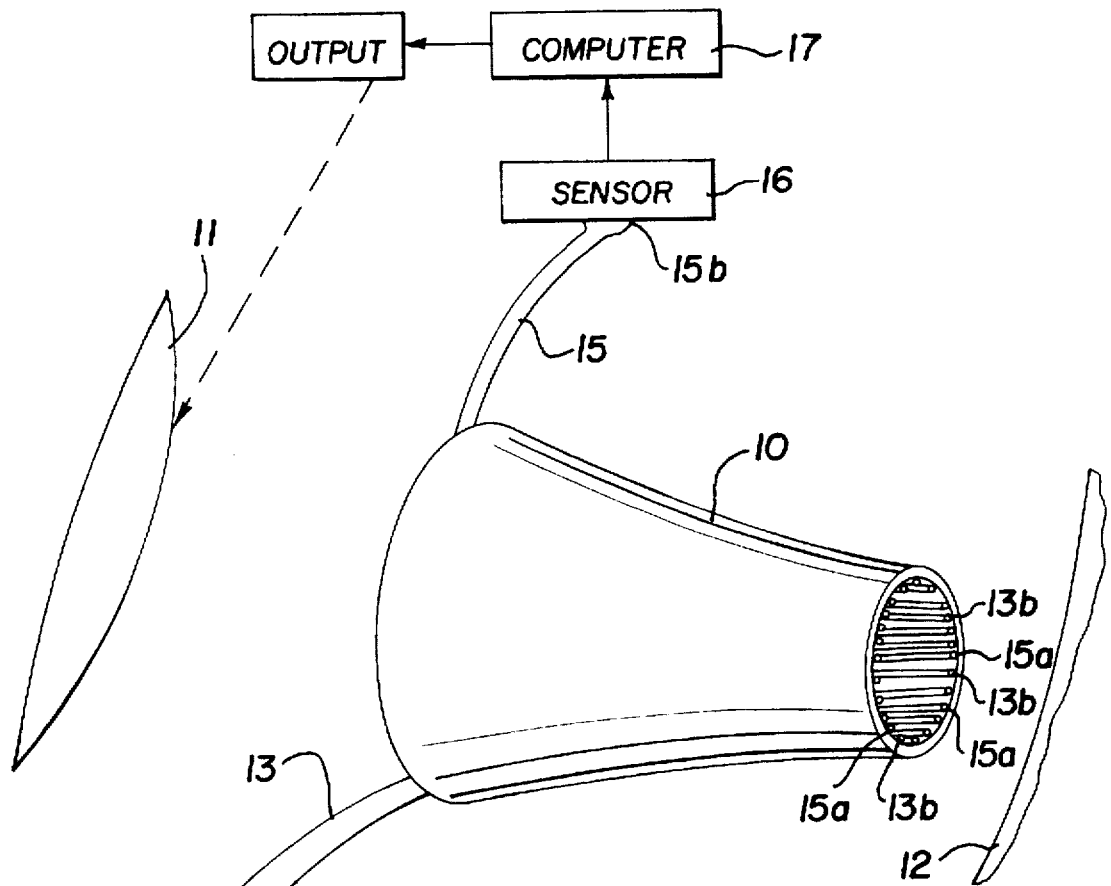
FIG. 1 is a schematic illustration of apparatus arranged to employ the principles of the invention.

As illustrated in FIG. 1 the apparatus includes a hollow viewing cone 10 supported by a suitable housing (not illustrated) and adapted for insertion into the ear canal. In the preferred embodiment the housing (not illustrated) also supports a viewing lens 11 aligned and positioned to permit the operator to visually observe a body 12 such as a tympanic membrane by looking through the viewing channel defined by the viewing lens 11 and the central axis of the viewing cone 10. Lens 11 may be a magnifying lens or the like, as desired.

In order to illuminate body 12 for viewing, a plurality of flexible optical fibers 13 are arranged so that the input ends 13a of fibers 13 are grouped to form the end face of an optical conduit arranged to receive visible wavelength energy emitted by an optical light source such as lamp 14. The opposite ends 13b of fibers 13 are arranged about the periphery (either inside or outside) of the insertion end of viewing cone 10 and thus arranged to direct visible wavelength energy from lamp 14 onto body 12. Such optical energy is reflected by body 12 to permit viewing of body 12 though lens 11 and viewing cone 10.

In order to simultaneously collect infrared energy radiating from body 12 without obstructing the viewing channel, a plurality of infrared-transmitting fibers or conduits 15 are arranged with the input ends 15a of the fibers 15 positioned about the periphery (either inside or outside) of the insertion end of viewing cone 10 to collect infrared radiation emitted by the body 12. The opposite ends 15b are grouped to form the end face of an infrared-transmitting conduit arranged to direct the collected infrared radiation onto an infrared sensor 16. The sensor 16 may be any of commonly known and used infrared sensors such as a thermopile, pyroelectric detector or the like. The output from the sensor 16 is fed to an appropriate computer 17 or other device which converts the detected signal to a graphic output representative of the temperature of the body as determined by the infrared radiation collected. Various sensors, devices and apparatus for converting the sensed radiation into digital or otherwise graphic representation of the sensed temperature are well known in the art.

As illustrated in FIG. 1, the graphic output may be displayed directly on the viewing lens 11 by means of a liquid crystal display or optically projected thereon. By appropriately arranging the first ends 15a of the infrared-transmitting fibers to receive only infrared radiation emitted by the body 12 directly in the line of sight through lens 11 along the viewing axis of the viewing cone 10, the observer can be assured that the temperature observed is, in fact, the temperature of the body visually observed. Furthermore, since the observation is visual and simultaneous with the temperature measurement, the operator may visually align the viewing cone 10 and ascertain that infrared radiation from only the tympanic membrane is being detected and that the optical path between the tympanic membrane and the input ends 15a of the infrared-transmitting fibers is unobstructed. By appropriately arranging the input ends 15a of the infrared transmitting fibers and the output ends 13b of the optical fibers 13, the body 12 can be illuminated and easily observed by the operator during the temperature measuring process.

Figure 2:
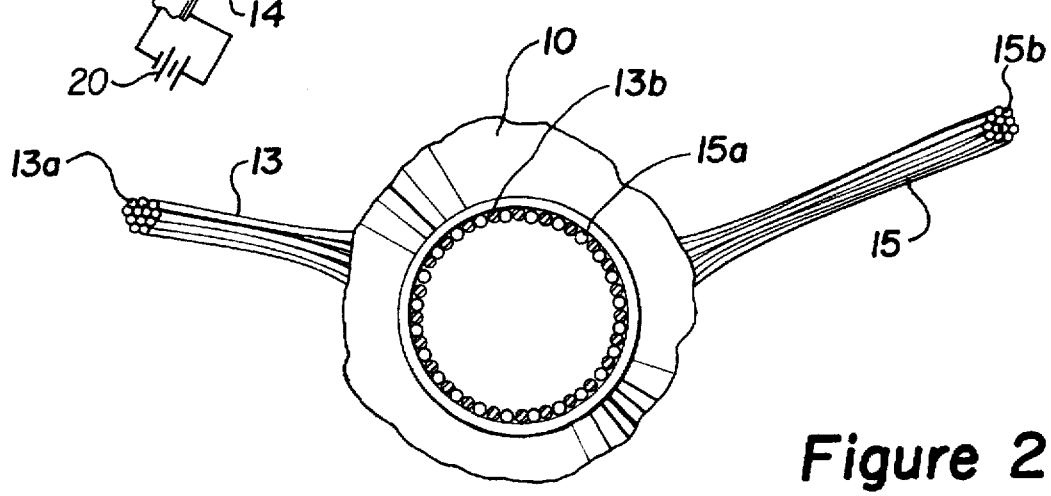
FIG. 2 is a representation of the arrangement of infrared wavelength conduits and visible wavelength conduits in a viewing cone in accordance with preferred embodiment of the invention.

The presently preferred arrangement of the optical fiber components of the invention is shown in FIG. 2 wherein the viewing cone 10 is shown in fragmentary portion as viewed from the insertion end for purposes of illustration. In the preferred embodiment, the input ends 15a of infrared-transmitting fibers 15 and the output ends 13b of optical fibers 13 are arranged in alternating sequence about the internal surface of the insertion end of the viewing cone 10. For clarity of illustration, the output ends 13b of the visible wavelength-transmitting fibers 13 are shaded. The opposite ends of the fibers 13 are grouped together to form a bundle of optical fibers which form an input face 13a positioned adjacent an optical source such as lamp 14 powered by a suitable source such as storage battery 20. The output ends 15b of infrared-transmitting fibers 15 are similarly grouped into a bundle to form an output end 15b for directing the collected infrared energy onto a detector or sensor 16.

Various well-known materials may be used for the optical wavelength conduits 13 and infrared-transmitting conduits 15. Plastic fibers and silicate glass fibers are well-known for conducting optical wavelengths by internal reflection. Furthermore, silicate glass effectively absorbs wavelengths longer than about 2.82 m. Thus, use of silicate glass fibers to transmit visible wavelengths to the membrane 12 avoids any artificial heating of the membrane by the illuminating light and prevents the infrared detector 16 from sensing infrared energy from the illumination source. Flexible conduits for transmitting infrared radiation can be readily fabricated from chalcogenide glasses based on selenium mixed with other elements such as germanium, arsenic, sulfur, tellurium, antimony and the like. Various such chalcogenide glasses can be fabricated into flexible rods or fibers which transmit radiation in the 2 to 14 μm range by internal reflection.

It will be recognized that the light conduit arrangement illustrated in the drawing may be varied as desired to produce the required results. For example, the visible wavelength conduits 13 and infrared-transmitting conduits 15 need not necessarily be the same size or positioned in alternate spaces about a circle. Bundles of fibers may be fabricated into ribbons which can be shaped about the inside, the outside or even used to form the viewing cone 10. It is only necessary that the conduits 13 transmit visible wavelengths from a remote source to the body 12 and that the conduits 15 collect infrared wavelengths emitted by the body and transmit that energy to an appropriate sensor, all without obstructing the visual observation path. It is to be understood, therefore, that the forms of the invention shown and described in detail are to be taken as preferred embodiments thereof. Various changes and modifications in form, arrangement of parts and the like may be resorted to without departing from the spirit and scope of the invention as defined by the appended claims.

What is claimed:

1. Apparatus for simultaneously illuminating and viewing a body while detecting infrared radiation emitted by the body comprising:

(a) a visible light source;

(b) an infrared radiation detector;

(c) a viewing channel arranged to permit optical viewing therethrough along a first axis in a first direction toward a body which emits infrared radiation;

(d) visible wavelength conduits operatively associated with said viewing channel, each having one end arranged to receive radiation from said visible light source and the other end arranged to radiate visible wavelength light substantially parallel with the axis of said viewing channel and toward said body;

(e) infrared wavelength conduits operatively associated with said viewing channel, each having one end arranged to receive infrared radiation from said body and direct said infrared radiation to said infrared radiation detector without obstructing the visual path through said viewing channel and (f) means for producing a graphic image representative of the temperature indicative of the infrared radiation directed onto said infrared radiation detector for display within said viewing channel.

2. Apparatus as defined in claim 1 wherein said infrared wavelength conduits are flexible fibers of chalcogenide glass.

3. Apparatus as defined in claim 1 wherein said visible wavelength conduits and said infrared wavelength conduits are glass fibers with input ends and output ends, the input ends of the visible wavelength conduits arranged to radiate visible wavelength light from a first end of the viewing channel and illuminate at least a portion of said body and the input ends of the infrared wavelength conduits arranged adjacent said first end of the viewing channel to collect infrared radiation emitted from the portion of said body illuminated by the visible wavelength light radiated from said visible wavelength conduits.

4. Apparatus for collecting infrared energy radiated by a body while simultaneously optically viewing the body comprising:

(a) a viewing assembly having a central axis adapted to permit visual observation of a body aligned with said central axis;

(b) a first conduit operatively associated with said viewing assembly arranged to transmit visible wavelength optical energy from a remote source toward said body in a direction substantially parallel with said central axis;

(c) a second conduit operatively associated with said viewing assembly arranged to receive infrared energy radiated by said body and transmit such infrared energy to a detector remote from said body;

(d) a lens comprising part of said viewing assembly and aligned with said central axis to permit optical viewing of said body through said lens;

(e) said detector being arranged to detect infrared energy transmitted thereto by said second conduit; and (f) means for producing a graphic image representative of the temperature of said body as indicated by the infrared energy radiated by said body and detected by said detector and displaying said graphic image through said lens.

* * * * *